United States Patent
Moretti et al.

(10) Patent No.: US 11,530,367 B2
(45) Date of Patent: Dec. 20, 2022

(54) ALDEHYDIC ODORANT

(71) Applicant: Firmenich SA, Satigny (CH)

(72) Inventors: Robert Moretti, Satigny (CH); Anthony Alexander Birkbeck, Satigny (CH); Christian Chapuis, Satigny (CH)

(73) Assignee: FIRMENICH SA, Meyrin (CH)

( * ) Notice: Subject to any disclaimer, the term of this patent is extended or adjusted under 35 U.S.C. 154(b) by 0 days.

(21) Appl. No.: 16/954,283

(22) PCT Filed: Mar. 26, 2019

(86) PCT No.: PCT/EP2019/057529
§ 371 (c)(1),
(2) Date: Jun. 16, 2020

(87) PCT Pub. No.: WO2019/185599
PCT Pub. Date: Oct. 3, 2019

(65) Prior Publication Data
US 2021/0095225 A1    Apr. 1, 2021

(30) Foreign Application Priority Data

Mar. 27, 2018  (EP) .................. 18164274

(51) Int. Cl.
*C11B 9/00* (2006.01)
*C07C 47/225* (2006.01)
(52) U.S. Cl.
CPC .......... *C11B 9/0034* (2013.01); *C07C 47/225* (2013.01); *C07C 2601/10* (2017.05)
(58) Field of Classification Search
CPC .................................................. C11B 9/0034
See application file for complete search history.

(56) References Cited

U.S. PATENT DOCUMENTS

| | | | |
|---|---|---|---|
| 6,376,458 B1 * | 4/2002 | Winter | C11B 9/0034 512/26 |
| 2011/0117046 A1 | 5/2011 | Levorse, Jr. et al. | |
| 2011/0217257 A1 | 9/2011 | Belko et al. | |
| 2013/0090390 A1 * | 4/2013 | Singer | C07C 47/225 514/772 |

FOREIGN PATENT DOCUMENTS

| | | |
|---|---|---|
| EP | 1054053 A2 | 11/2000 |
| WO | 2017046071 A1 | 3/2017 |

OTHER PUBLICATIONS

Coriander odor descriptor non-patent literature obtained Apr. 25, 2022 at: http://www.thegoodscentscompany.com/odor/coriander.html#first (Year: 2022).*
International Search Report and Written Opinion for International Patent Application No. PCT/EP2019/057529, dated Apr. 24, 2019, 11 pages.
Bône et al.: "Microencapsulated Fragrances in Melamine Formaldehyde Resins", CHIMIA 2011, 65, No. 3, pp. 177-181.

\* cited by examiner

*Primary Examiner* — Arrie L Reuther
(74) *Attorney, Agent, or Firm* — Armstrong Teasdale LLP

(57) ABSTRACT

Described herein is compound of formula (I)

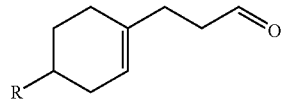

in the form of any one of its stereoisomers or as a mixture thereof, wherein R represents a n-butyl or a (3-methylbutan-2-yl) group. The use of the compound of formula (I) as perfuming ingredient of the aldehydic type and the compound as part of a perfuming composition or of a perfumed consumer product are also described.

9 Claims, No Drawings

ALDEHYDIC ODORANT

CROSS-REFERENCE TO RELATED APPLICATIONS

This application is a U.S. National Phase Application of International Patent Application No. PCT/EP2019/057529, filed Mar. 26, 2019, which claims the benefit of priority to European Patent Application No. 18164274.5, filed Mar. 27, 2018, the entire contents of each of which are hereby incorporated by reference herein.

TECHNICAL FIELD

The present invention relates to the field of perfumery. More particularly, it concerns the compound of formula (I) as defined herein below, and its uses as perfuming ingredient. Therefore, following what is mentioned herein, the present invention comprises the invention compound as part of a perfuming composition or of a perfumed consumer product.

PRIOR ART

In the perfumery industry, there is a constant need to provide compounds imparting novel organoleptic notes. In particular, there is an interest towards aldehydic notes which represent one of the key organopleptic facets of the lily of the valley odor. So, compounds imparting said note are particularly sought after to reconstitute the delicate floral odor of muguet which does not survive even the mildest of extraction methods to yield an essential oil.

The present invention provides a novel perfumery ingredient of formula (I), which has never been previously reported, which could be used to bring one facet of the muguet note, imparting a very interesting organoleptic note combining aldehydic, creamy and coriander characteristics.

To the best of our knowledge, similar structural analogues as perfuming ingredients are described in US 20110217257 and US 20110117046 wherein 3-(4-alkyl)cyclohexanepropanal compounds imparting a floral, muguet green note are reported while EP 1054053 discloses 3-(4-tert-butyl-1-cyclohexen-1-yl)propanal also known as Mugoxal® (trademark from Firmenich SA, Suisse) as having a the lily of the valley odor type. Said prior art compounds possess organoleptic properties different from compound of formula (I).

Therefore, none of these prior art documents reports or suggests any organoleptic properties of the compounds of formula (I), or any use of said compounds in the field of perfumery.

SUMMARY OF THE INVENTION

The invention relates to compound of formula (I) imparting an aldehydic note characteristic of one aspect of the complex lily of the valley odor while possessing a creamy and coriander note.

So, a first object of the present invention is the use of a compound of formula (I),

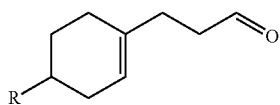

(I)

in the form of any one of its stereoisomers or as a mixture thereof, and wherein R represents a n-butyl or a (3-methylbutan-2-yl) group.

A second object of the present invention is a method to confer, enhance, improve or modify the odor properties of a perfuming composition or of a perfumed article, which method comprises adding to said composition or article an effective amount of at least a compound of formula (I) as defined above.

A third object of the present invention is a compound of formula (I) as defined above.

Another object of the present invention is a perfuming composition comprising
i) at least one compound of formula (I), as defined above;
ii) at least one ingredient selected from the group consisting of a perfumery carrier and a perfumery base; and
iii) optionally at least one perfumery adjuvant.

A last object of the present invention is a perfumed consumer product comprising at least one compound of formula (I) or a composition as defined above.

DESCRIPTION OF THE INVENTION

Surprisingly, it has now been discovered that a compound of formula (I) possesses the aldehydic facet of the lily of the valley odor note in combination with creamy and coriander notes. Said compound of formula (I) could be used in perfume composition reconstituting the muguet odor.

A first object of the present invention is a compound of formula

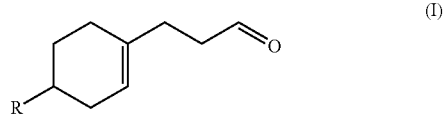

(I)

in the form of any one of its stereoisomers or as a mixture thereof, and wherein R represents a n-butyl or a (3-methylbutan-2-yl) group. Said compound can be used as perfuming ingredient, for instance to impart odor notes of the aldehydic, coriander and creamy type with lily and the valley aspect.

For the sake of clarity, by the expression "any one of its stereoisomers", or the similar, it is meant the normal meaning understood by a person skilled in the art, i.e. that the invention's compound can be a pure enantiomer (if chiral), a mixture of enantiomers (mixture of stereoisomers), a pure diastereomer, a mixture of diastereoisomers; or a mixture thereof.

According to any one of the above embodiments of the invention, said compound (I) is a $C_{13}$-$C_{14}$ compound.

According to any one of the above embodiments of the invention, R represents a n-butyl or a (3-methylbutan-2-yl) group. Preferably, R represents a n-butyl group.

As specific examples of the invention's compounds, one may cite, as non-limiting example, 3-(4-n-butyl-1-cyclohexen-1-yl)propanal which is characterized by having an aldehydic note characteristic of the lily of the valley odor note along with creamy note and coriander note, in particular coriander leaf notes, and also comprising a mandarin facet and freshness aspect. Said compound possesses also a fatty and watery character strongly reminiscent of the very well-known ingredient, Lilial® (2-methyl-3-[4-(2-methyl-2-propanyl)phenyl]propanal, trademark from Givaudan-Roure SA, Vernier, Suisse). The overall organoleptic effect provided by this compound is very powerful with a bloom effect (diffusion).

As other example, one may cite 3-[4-(1,2-dimethylpropyl)-1-cyclohexen-1-yl]propanal, which possesses an odor similar to the one mentioned above but slightly less powerful.

The invention's compound is surprisingly very powerful. All of the comparative compounds cited above, being structurally close to the invention compound, impart a less interesting odor note with metallic and/or fatty notes and lacking radiance. Only the invention's compound is devoid of metallic and fatty notes.

TABLE 1

Comparative compounds and their odor properties

| Compound structure and name | Odor notes |
|---|---|
| 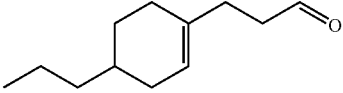<br>3-(4-n-propylcyclohex-1-en-1-yl)propanal | Aldehydic, seal, grease, oily |
| 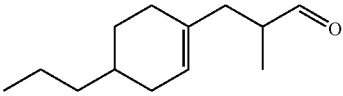<br>2-methyl-3-(4-n-propylcyclohex-1-en-1-yl)propanal | Fatty, fried, aldehydic |
| 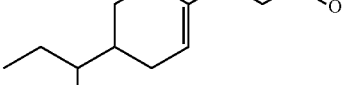<br>3-(4-(sec-butyl)cyclohex-1-en-1-yl)propanal | Aldehydic, fatty |
| 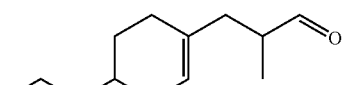<br>3-(4-(sec-butyl)cyclohex-1-en-1-yl)-2-methylpropanal | Dirty, fatty |
| 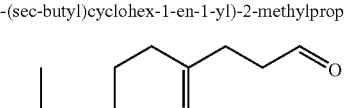<br>3-(4-isobutylcyclohex-1-en-1-yl)propane | Aldehydic, oily, rancid |
| 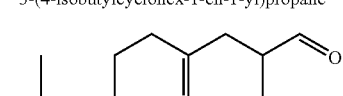<br>3-(4-isobutylcyclohex-1-en-1-yl)-2-methylpropanal | Aldehydic, fried, metallic |
| 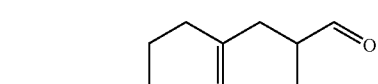<br>3-(4-n-butylcyclohex-1-en-1-yl)-2-methylpropanal | Aldehydic, fatty, metallic |
| 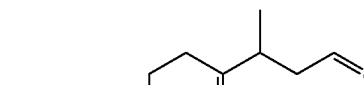<br>3-(4-n-butylcyclohex-1-en-1-yl)butanal | Aldehydic, green, dusty |

TABLE 1-continued

Comparative compounds and their odor properties

| Compound structure and name | Odor notes |
|---|---|
| 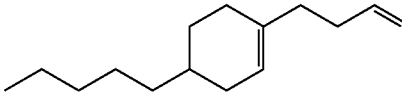<br>3-(4-n-pentylcyclohex-1-en-1-yl)propanal | Aldehydic, fatty, fried |
| 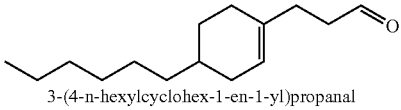<br>3-(4-n-hexylcyclohex-1-en-1-yl)propanal | Aldehydic, fried, metallic |

According to a particular embodiment of the invention, the compounds of formula (I) may be selected from the group consisting of 3-(4-n-butyl-1-cyclohexen-1-yl)propanal, and 3-[4-(1,2-dimethylpropyl)-1-cyclohexen-1-yl]propanal. Preferably, the compounds of formula (I) may be 3-(4-n-butyl-1-cyclohexen-1-yl)propanal.

When the odor of the invention's compounds is compared with that of the prior art compounds Mugoxal® (3-(4-tert-butyl-1-cyclohexen-1-yl)propanal; origin: Firmenich SA, Geneva, Switzerland) or Starfleur® (3-[4-(2-Methylpropyl)cyclohexyl]propanal; origin: International Flavors & Fragrances, USA), then the invention's compounds distinguish themselves by a more powerful aldehydic with creamy and coriander characteristic notes and by lacking the floral note of Mugoxal® and the citronella note of Starfleur®. 3-(4-n-butylcyclohexyl) propanal, reported in US 20110117046, does not possess the typical floral note odor of the invention's compound but imparts undesired fatty and metallic odor notes. The odor of the invention's compounds is much fresher than the prior art compounds. Moreover, the invention's compound possesses a blooming effect and diffusion/radiance which are not present in the prior art compounds.

Said differences lend the invention's compounds and the prior art compounds to be each suitable for different uses, i.e. to impart different organoleptic impressions.

As mentioned above, the invention concerns the use of a compound of formula (I) as a perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note. Understood that the final hedonic effect may depend on the precise dosage and on the organoleptic properties of the invention's compound, but anyway the addition of the invention's compound will impart to the final product its typical touch in the form of a note, touch or aspect depending on the dosage.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;

ii) at least one ingredient selected from the group consisting of a perfumery carrier and a perfumery base; and iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bone et al. Chimia, 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin.

In particular one may cite perfuming co-ingredients knows for having a similar olfactive note, such as:

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: *eucalyptus* oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients:Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4 (2H)-pyranol, beta ionone, methyl 2-(methylamino) benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methyl-ionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;

Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2, 2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3, 4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound (I) is added. Consequently, another object of the present invention consists of by a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface).

In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. In the case of perfumed consumer product, typical concentrations are in the order of 0.001% to 1% by weight, or even more, of the compounds of the invention based on the weight of the consumer product into which they are incorporated.

The compound of formula (I) can be prepared according to a method as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) using either a Bruker Advance II Ultrashield 400 plus operating at (400 MHz ($^1H$) and 100 MHz ($^{13}C$) or a Bruker Advance III 500 plus operating at (500 MHz ($^1H$) and 125 MHz ($^{13}C$) or a Bruker Advance III 600 cryoprobe operating at (600 MHz ($^1H$) and 150 MHz ($^{13}C$). Spectra were internally referenced and chemical shifts δ are indicated in ppm relative to TMS 0.0 ppm and coupling constants J are expressed in Hz.

Example 1

Synthesis of 3-(4-n-butylcyclohex-1-en-1-yl)propanal (Compound of Formula (I))

a) Preparation of 8-butyl-1-oxaspiro[4.5]decan-2-one 4-n-Butylcyclohexanol (175 g; 1120 mmol) was placed in a 1.5 1, 4 necked flask equipped with 2 addition funnels, thermometer and a Dean-Stark apparatus. The alcohol was heated under $N_2$ at 155° C. and n-butyl acrylate (85 g; 660 mmol) and di-tert-butyl peroxide (39.3 g; 264 mmol) were added simultaneously but separately to the reaction. The internal temperature was initially at 158° C., but slowly diminished as the additions proceeded, so the bath temperature was slowly raised to 165° C. in order to restore an internal temperature of 155° C. During the process a liquid (t-butanol) distilled (vapor temp-=79-81° C.). The addition took 6 h and 39 ml of t-butanol was collected. The reaction was cooled to 50° C. MTBE (200 ml) was added, followed by 30% aq. NaOH (50 g NaOH dissolved in 110 ml $H_2O$). The mixture was stirred for 30 minutes, then water (200 ml) and more MTBE (200 ml) were added. The mixture was cooled to RT and transferred to a 2 liter separating funnel. Diethyl ether (500 ml) and water (400 ml) were added and the mixture vigorously shaken. Phases were separated. The aqueous phase was re-extracted with diethyl ether (500 ml). Each organic phase was treated with water (300 ml). The organic phase (containing the excess of 4-n-butylcyclohexanol) was dried over sodium sulfate, filtered and concentrated and distilled (bulb-to-bulb; 90° C./1 mbar) to give 61 g (390 mmol) of recovered 4-n-butylcyclohexanol.

The aqueous phase (containing the sodium salt of the hydroxy-carboxylic acid) was acidified with 50% aq. $H_2SO_4$ (400 ml, this protonated the salt of the acid which then formed the lactone) and extracted with diethyl ether (2×750 ml). Each org. phase was washed with water (2×1 liter), aq. sat. $NaHCO_3$. Combined organic fractions were dried over sodium sulfate. GC of the crude mixture showed 11% of starting material and 84% product. Most of the starting material was distilled off by bulb-to-bulb distillation (80-105° C./0.028 mbar). 8-butyl-1-oxaspiro[4.5]decan-2-one was distilled at 130° C./0.028 mbar), giving two fractions:
Fraction #1: 49.21 g; 100% pure by GC; 39:61 mixture of diastereoisomers
Fraction #2: 1.87 g; 89% pure by GC; 15:85 mixture of diastereoisomers
Overall yield: 242 mmol; 37%

¹H-NMR: δ0.89 (t J 7 Hz, 3H); 0.98-1.08 (m, 1H); 1.19-1.39 (m, 8H); 1.48 (m, 1H); 1.60-1.91 (m, 5H); 1.89 (t, J 7 Hz, 0.8H); 2.057 (t, J 7 Hz, 1.2H); 2.58 (m, 2H) ppm.
¹³C-NMR: δ 14.08 (q); 14.11 (q); 22.89 (t); 22.94 (t); 28.63 (t); 28.66 (t); 29.17 (t); 29.37 (t); 29.41 (t); 30.60 (t); 34.14 (t); 35.64 (t); 35.94 (t); 36.10 (d); 36.30 (t); 36.40 (d); 36.87 (t); 85.94 (s); 87.29 (s); 176.71 (s); 176.93 (s) ppm.

b) Preparation of butyl 3-(4-butylcyclohex-1-en-1-yl)propanoate

In a 500 ml flask equipped with a short Vigreux column, Dean-Stark trap and condenser, 8-butyl-1-oxaspiro[4.5]decan-2-one (50.9 g; 242 mmol) and 1-butanol (89.7 g; 1210 mmol) were mixed. Concentrated sulfuric acid (1.19 g; 12 mmol) was added and the solution heated in an oil bath at 150° C. for 9 h. 1-Butanol was evaporated and the residue diluted with n-pentane (500 ml). The solution was washed with aqueous saturated solution of NaHCO₃ and brine (300 ml each). Aqueous phases were extracted with n-pentane (300 ml). The combined extracts were dried over sodium sulfate and filtered. The product was purified by bulb-to-bulb distillation (132-160° C./0.046 mbar).
Fraction #1: 4.46 g; 95% by GC
Fraction #2: 56.42 g; 95% by GC
Fraction #3: 1.9 g; 71% by GC
Overall yield: 222 mmol; 92%
¹H-NMR: δ 0.89 (t, J 7 Hz, 3H); 0.93 (t, J 7.5 Hz, 3H); 1.14-1.32 (m, 7H); 1.34-1.47 (m, 3H); 1.55-1.64 (m, 3H); 1.71-1.77 (m, 1H); 1.88-2.11 (m, 3H); 2.23-2.28 (m, 2H); 2.38-2.43 (m, 2H); 4.07 (d, J 7 Hz, 2H); 5.38 (m, 1H) ppm.
¹³C-NMR: δ 13.73 (q); 14.15 (q); 19.17 (t); 22.98 (t); 28.37 (t); 29.27 (t); 29.28 (t); 30.74 (t); 32.05 (t); 32.73 (t); 32.97 (t); 33.39 (d); 36.18 (t); 64.16 (t); 121.15 (d); 135.99 (s); 173.72 (s) ppm.

c) Preparation of 3-(4-butylcyclohex-1-en-1-yl)propanal

Diisobutylaluminum hydride (1M in dichloromethane, 241 ml; 241 mmol) was added dropwise to a solution of 8-butyl-1-oxaspiro[4.5]decan-2-one (56.42 g; 95%; 201 mmol) in dry dichloromethane (500 ml) at −70° C. under N₂ (over 1 h30). The reaction was further stirred at −70° C. for 2 h30, then quenched by slow addition of a 10% aqueous solution of Na/K tartrate (Rochelle's salt; 700 g). A very efficient stirring required at this stage. The reaction was warmed up to RT and stirred overnight. The phases were separated. The aqueous phase was extracted with dichloromethane. Each organic phase was washed with brine. Combined extracts were dried over sodium sulfate and filtered. The product was purified by column chromatography on silica gel (eluent: heptane/ethyl acetate 15:1 to 10:1) followed by bulb-to-bulb distillation (80° C./0.04 mbar).
Yield: 30 g (154 mmol); 77%
¹H-NMR: δ0.89 (t, J7 Hz, 3H); 1.15-1.33 (m, 7H); 1.39-1.48 (m, 1H); 1.56-1.64 (m, 1H); 1.72-1.78 (m, 1H); 1.88-2.12 (m, 3H); 2.28 (m, 2H); 2.49-2.54 (m, 2H); 5.39 (m, 1H); 9.76 (t, J 1.9 Hz, 1H) ppm.
¹³C-NMR: δ14.14 (q); 22.96 (t); 23.23 (t); 28.58 (t); 29.25 (t); 29.86 (t); 32.02 (t); 33.38 (d); 36.14 (t); 41.92 (t); 121.54 (d); 135.60 (s); 202.78 (d) ppm.

Example 2

Synthesis of 3-(4-(sec-butyl)cyclohex-1-en-1-yl) propanal (Comparative Compound)

a) Preparation of 1-(2-(1,3-dioxolan-2-yl)ethyl)-4-(sec-butyl)cyclohexan-1-ol

A solution of 2-(2-bromoethyl-1,3-dioxolane) (18.0 g, 100 mmol) in THF was added slowly dropwise to a stirred suspension of Mg (2.7 g, 112 mmol) in THF (100 mL). Mg activated with MgBr₂ (ca. 100 mg) and or some iodine crystals. Once exothermic the bromide was added slowly dropwise and the temperature allowed to rise, to 50-60° C., then allowed to cool to 30° C. A solution of the 4-(sec-butyl)cyclohexan-1-one (100 mmol) in THF (20 mL) was then added slowly dropwise. Temperature during addition <35° C. The solution was stirred for a further 4 hours at ambient temperature then poured into a stirred mixture of saturated ammonium chloride and ice (1:1, 200 mL), re-extracted with EtOAc (2×100 mL), washed with saturated sodium bicarbonate (100 mL), then brine (100 mL), dried over MgSO₄, filtered and the solvents removed in vacuo. The crude alcohol as a mixture of cis and trans isomers was used directly in the next step without further purification.

b) Preparation of 2-(2-(4-sec-butyl)cyclohex-1-en-1-yl)ethyl)-1,3-dioxolane

POCl₃ (4.4 g, 28.5 mmol), was added slowly dropwise to a stirred solution of the alcohol obtained in step a) (4.8 g, 19 mmol) in pyridine (25 mL) cooled to 0° C. The suspension was stirred at 0° C. for 30 mins then allowed to warm to ambient temperature and stirred for a further 1 hr. The suspension was then poured into ice/water, extracted with EtOAc (2×100 mL), washed with saturated sodium bicarbonate until neutral, then washed with 10% H₂SO₄, brine, dried over MgSO₄, filtered and the solvents removed in vacuo. The crude dioxolane was further purified by bulb to bulb (Kugelrohr) distillation to give the pure dioxolane, 3.5 g.
¹H (400 MHz): δ 0.78-0.90 (m, 6H), 1.06-1.31 (m, 3H), 1.32-1.49 (m, 2H), 1.64-1.80 (m, 4H), 1.88-2.09 (m, 4H), 3.81-3.90 (m, 2H), 3.91-4.01 (m, 2H), 4.86 (t, J 4.9, 1H), 5.42 (bs, 1H) ppm.
¹³C (100 MHz): δ 11.7, 11.8, 15.4, 15.8 (q), 25.5, 26.4, 26.7, 27.2, 27.6, 29.2, 29.3, 29.6, 32.2, 32.3 (t), 38.0, 38.3, 38.8, 39.0 (d), 64.9 (t), 104.5 (d), 121.0, 121.1 (d), 136.8 (s) ppm.

c) Preparation of 3-(4-(sec-butyl)cyclohex-1-en-1-yl)propanal

The dioxolane obtained in step b) (3.4 g, 14.4 mmol) was dissolved in acetone (45 mL) and water (15 mL) and concentrated HCl (0.5 mL) was added, then the mixture heated under reflux for 15 hrs. The mixture was then cooled, diluted in Et₂O (100 mL), the aqueous phase re extracted with Et₂O (100 mL). The combined organic extract was then washed with saturated sodium bicarbonate (2×50 mL), brine (50 mL), dried over MgSO₄, filtered and the solvents removed in vacuo to yield the crude aldehyde. Further purification by bulb to bulb distillation gave the desired aldehyde, 2.5 g.
¹H (400 MHz): δ 0.83 (t, J 6.4, 3/2H), 0.86 (t, J 7.2, 3/2H), 1.09-1.32 (m, 4H), 1.33-1.47 (m, 3H), 1.66-1.82 (m, 3H), 1.88-2.02 (m, 3H), 2.28 (t, J 7.4, 2H), 2.49-2.54 (m, 2H), 5.41 (bs, 1H), 9.76 (t, J 2.0, 1H) ppm.
¹³C (100 MHz): δ 11.7, 11.8, 15.4, 15.8 (q), 25.4, 26.4, 26.7, 27.0, 27.6, 29.3 29.4, 29.5, 29.8 (t), 37.9, 38.2, 38.7, 38.9 (d), 41.9 (t), 121.9, 122.0 (d), 135.6 (s), 202.8 (d) ppm.

Example 3

Synthesis of 3-[4-(1,2-dimethylpropyl)-1-cyclohexen-1-yl]propanal (Compound of Formula (I))

3-[4-(1,2-dimethylpropyl)-1-cyclohexen-1-yl]propanal was prepared following the experimental part reported in Example 2 by replacing, in the first step, 4-(sec-butyl)cyclohexan-1-one with 4-(3-methylbutan-2-yl)cyclohexan-1-one.

2-(2-(4-(3-methylbutan-2-yl)cyclohex-1-en-1-yl)ethyl)-1,3-dioxolane $^1$H (400 MHz): δ 0.72-0.81 (m, 6H), 0.88 (d, J 2.6, 3/2H), 0.91 (d, J 2.6, 3/2H), 1.00-1.31 (m, 3H) 1.38-1.53 (m, 2H), 1.62-1.83 (m, 5H), 1.90-2.10 (m, 4H), 3.82-3.87 (m, 2H), 3.94-3.99 (m, 2H), 4.86 (t, J 4.9, 1H), 5.41 (bs, 1H) ppm.
$^{13}$C (100 MHz): δ 11.0, 11.3, 17.4, 17.8, 21.8, 21.9 (q), 25.8, 27.9, 28.1 (t), 28.8, 29.0 (d), 29.1, 29.2, 30.7 31.8, 32.2 (t), 36.2 36.4, 43.1, 43.5 (d), 64.9 (t), 104.5, 121.0 (d), 136.7, 136.8 (s) ppm.

3-(4-(3-methylbutan-2-yl)cyclohex-1-en-1-yl)propanal $^1$H (400 MHz): δ 0.73-0.81 (m, 6H), 0.88 (d, J 2.2, 3/2H), 0.90 (d, J 2.2, 3/2H), 1.02-1.32 (m, 3H), 1.38-1.53 (m, 1H), 1.62-1.84 (m, 3H), 1.88-2.06 (m, 3H), 2.28 (t, J 7.4, 2H), 2.49-2.55 (m, 2H), 5.41 (bs, 1H), 9.76 (t, J 1.9, 1H) ppm.
$^{13}$C (100 MHz): δ 11.0, 11.3, 17.4, 17.8, 21.7, 21.8 (q), 25.7, 27.8, 28.1 (t), 28.8, 28.9 (d), 29.2, 29.3, 29.7, 30.6 (t), 36.1, 36.3 (d), 41.9 (t), 43.0, 43.4 (d), 121.9 (d), 135.5, 135.6 (s), 202.8 (d) ppm.

Example 4

Synthesis of 3-(4-n-propylcyclohex-1-en-1-yl)propanal (Comparative Compound)

3-(4-propylcyclohex-1-en-1-yl)propanal was prepared following the experimental part reported in Example 2 by replacing, in the first step, 4-(sec-butyl)cyclohexan-1-one with 4-propylcyclohexan-1-one.

2-(2-(4-Propylcyclohex-1-en-1-yl)ethyl)-1,3-dioxolane 2-(2-(4-Propylcyclohex-1-en-1-yl)ethyl)-1,3-dioxolane was obtained in 81% yield.
IR: 2954, 2910, 2872, 1465, 1450, 1407, 1378, 1360, 1130, 1035, 963, 940, 916, 891, 807, 737.
$^1$H-NMR: δ0.90 (t, J=7.2, 3H); 1.16-1.26 (m, 3H); 1.30-1.36 (m, 2H); 1.44-1.50 (m, 1H); 1.57-1.63 (m, 1H); 1.72-1.77 (m, 3H); 1.90-2.0 (m, 2H); 2.0-2.09 (m, 3H); 3.83-3.87 (m, 2H); 3.95-3.99 (m, 2H); 4.86 (t, J=4.7, 1H); 5.40 (brs, 1H) ppm.
$^{13}$C-NMR (100 MHz): δ 14.4 (q); 20.1 (t), 28.5 (t); 29.4 (t); 31.9 (t); 32.0 (t); 32.2 (t); 33.2 (t); 38.8 (t); 64.9 (2t); 104.5 (d); 120.6 (d); 136.8 (s) ppm.

3-(4-propylcyclohex-1-en-1-yl)propanal 3-(4-n-propylcyclohex-1-en-1-yl)propanal was obtained in 74% yield.
IR: 2955, 2911, 2872, 2833, 2715, 1725, 1464, 1454, 1437, 1411, 1388, 1378, 1053, 916, 804, 737.
$^1$H (400 MHz): δ 0.89 (t, J=7.3, 3H); 1.15-1-27 (m, 3H); 1.33 (brhex, J=7.3, 2H); 1.42-1-50 (m, 1H); 1.56-1.65 (m, 1H); 1.72-1.77 (m, 1H); 1.91 (brd, J=17, 1H); 1.95-2.03 (m, 1H); 2.08 (brd, J=17, 1H); 2.28 (t, J=7.5, 2H); 2.50-2.54 (m, 2H); 5.39 (brs, 1H); 9.76 (t, J=1.9, 1H) ppm.
$^{13}$C (100 MHz): δ 14.3 (q); 20.1 (t); 28.6 (t); 29.2 (t); 29.8 (t); 31.9 (t), 33.1 (d), 38.7 (t);
41.9 (t); 121.5 (d); 135.6 (s), 202.8 (d) ppm.

Example 5

Synthesis of 2-methyl-3-(4-propylcyclohex-1-en-1-yl)propanal (Comparative Compound)

2-methyl-3-(4-propylcyclohex-1-en-1-yl)propanal was prepared following the experimental part reported in Example 2 by replacing, in the first step, 4-(sec-butyl)cyclohexan-1-one with 4-propylcyclohexan-1-one and 2-(2-bromoethyl-1,3-dioxolane with 2-(1-bromopropan-2-yl)-1,3-dioxolane (prepared according to JP 2016084325).

2-(1-(4-propylcyclohex-1-en-1-yl)propan-2-yl)-1,3-dioxolane 2-(1-(4-propylcyclohex-1-en-1-yl)propan-2-yl)-1,3-dioxolane was obtained in 76% yield in a form of a 1:1 mixture of stereoisomers.
IR: 2956, 2910, 2872, 1456, 1436, 1397, 1376, 1157, 1133, 1108, 1080, 1059, 1039, 997, 966, 940, 915, 800.
$^1$H-NMR: δ 0.85 (d, J=6.8, 3H); 0.89 (t, J=7.3, 3H); 1.15-1.25 (m, 3H); 1.33 (hept, J=7.1, 2H); 1.41-1.52 (m, 1H); 1.57-1.65 (m, 1H); 1.71-1.80 (m, 2H); 1.84-2.00 (m, 3H); 2.08 (brd, J=16, 1H); 2.15-2.23 (m, 1H); 3.84-3.96 (m, 4H); 4.69 (d, J=4.1, 0.5H); 4.70 (d, J=3.9, 0.5H); 5.39 (brs, 1H).
$^{13}$C-NMR (100 MHz): δ 13.3, 13.1 (q); 14.4, 14.4 (q); 20.1, 20.1 (t); 28.4, 28.0 (t); 29.4, 29.4 (t); 32.1, 32.2 (t); 33.1, 33.3 (d); 34.7, 34.9 (d); 40.0, 39.6 (t); 38.9, 38.7 (t); 65.1 (2t); 107.5, 107.4 (d); 122.5, 122.5 (d); 135.3, 135.3 (s) ppm.

2-methyl-3-(4-propylcyclohex-1-en-1-yl)propanal 2-methyl-3-(4-propylcyclohex-1-en-1-yl)propanal dioxolane was obtained in 75% yield in a form of a 1:1 mixture of diastereoisomers.
IR: 2956, 2911, 2872, 2835, 2706, 1726, 1455, 1435, 1394, 1376, 1139, 916, 795.
$^1$H (400 MHz): δ 0.89 (t, J=7.3, 3H); 1.04 (d, J=7.1, 3H); 1.15-1.25 (m, 2H); 1.33 (hex, J=7.4, 2H); 1.42-1.51 (m, 1H); 1.54-1.65 (m, 2H); 1.72-1.77 (m, 1H); 1.86-2.01 (m, 3H); 2.09 (brd, J=17, 1H); 2.34-2.40 (m, 1H); 2.47-2.54 (m, 1H); 5.42 (brs, 1H); 9.60 (d, J=2.6, 1H) ppm.
$^{13}$C (100 MHz): δ 13.2, 13.4 (q); 14.4 (q); 20.1 (t); 28.3, 28.4 (t); 29.1, 29.2 (t); 32.1, 32.0 (t), 33.0, 33. (d); 38.6, 38.7 (t); 38.9, 39.0 (t), 44.3, 44.4 (d); 123.5, 123.6 (d); 134.0, 134.1 (s), 205.4 (d) ppm.

Example 6

Synthesis of 3-(4-(sec-butyl)cyclohex-1-en-1-yl)-2methylpropanal (Comparative Compound)

3-(4-(sec-butyl)cyclohex-1-en-1-yl)-2methylpropanal was prepared following the experimental part reported in Example 2 by replacing, in the first step, 2-(2-bromoethyl-1,3-dioxolane with 2-(1-bromopropan-2-yl)-1,3-dioxolane (prepared according to JP 2016084325).

2-(1-(4-sec-butyl)cyclohex-1-en-1-yl)propan-2-yl)-1,3-dioxolane 2-(1-(4-sec-butyl)cyclohex-1-en-1-yl)propan-2-yl)-1,3-dioxolane was obtained in 50% yield in a form of a 1:1:1:1 mixture of diastereoisomers.

IR: 2959, 2914, 2874, 2838, 1460, 1436, 1397, 1377, 1218, 1157, 1136, 1108, 1081, 1057, 1039, 998, 941, 911, 847, 801, 722.

$^1$H (400 MHz): δ 0.81-0.89 (m, 9H); 1.08-1.30 (m, 3H); 1.35-1.45 (m, 2H); 1.65-1.83 (m, 3H); 1.85-2.00 (m, 4H); 2.15-2.23 (brt, J=14, 1H); 3.82-3.89 (m, 2H); 3.91-3.98 (m, 2H); 4.69 (d, J=4.0, 0.5H); 4.71 (d, J=3.9, 0.5H); 5.41 (brs, 1H) ppm.

$^{13}$C (100 MHz): δ 11.8, 11.7 (q); 13.4, 13.1 (q); 15.8, 15.8 (q); 25.6, 25.5 (t); 26.4, 26.4, 26.7, 26.7 (t); 27.8, 27.7, 28.9, 28.8 (t); 29.1, 29.0, 29.6, 29.6 (t); 34.9, 34.6 (d); 38.1, 38.1, 38.4, 38.3 (d); 38.8, 38.7, 39.1, 39.0 (d); 40.0, 39.5 (t); 65.1 (2t); 107.5, 107.3 (d); 123.0, 122.9 (d); 135.4, 135.3, (s) ppm.

3-(4-(sec-butyl)cyclohex-1-en-1-yl)-2methylpropanal 3-(4-(sec-butyl)cyclohex-1-en-1-yl)-2methylpropanal was obtained in 81% yield in a form of a 1:1:1:1 mixture of stereoisomers.

IR: 2960, 2916, 2874, 2836, 2707, 1726, 1455, 1435, 1393, 1377, 1145, 912, 797.

$^1$H (400 MHz): δ 0.81-0.89 (m, 6H); 1.04 (d, J=6.8, 3H); 1.09-1.32 (m, 4H); 1.34-1.46 (m, 2H); 1.66-1.83 (m, 2H); 1.87-2.02 (m, 3H); 2.33-2.40 (m, 1H); 2.46-2.54 (m, 1H); 5.44 (brs, 1H); 9.61 (d, J=2.5, 1H) ppm.

$^{13}$C (100 MHz): δ 11.7, 11.8 (q); 13.2, 13.4 (q); 15.4, 15.8 (q), 25.3, 25.4, 26.4, 26.7 (t); 27.0, 27.1, 27.6, 27.7 (t); 29.1, 29.2 (t); 29.5, 29.6 (t); 37.9, 38.0, 38.2, 38.2 (d); 38.7, 38.7, 38.9, 38.9 (d); 39.8, 38.9 (t); 44.3, 44.4 (d); 123.9, 124.0, 124.1, 124.1 (d); 134.0, 134.0 (s); 205.4, 205.4 (d) ppm.

Example 7

Synthesis of 3-(4-n-butylcyclohex-1-en-1-yl)-2-methylpropanal (Comparative Compound)

55% Formaldehyde (Formcel, 0.9 g; 16.5 mmol), 40% aqueous dimethylamine (0.15 g; 1.33 mmol) and propionic acid (0.4 g; 5.4 mmol) were heated at 90° C. under N$_2$. 3-(4-butylcyclohex-1-en-1-yl)propanal obtained in example 1 (2 g; 10.3 mmol) was added. After 10 minutes, the reaction was cooled to room temperature, diluted with MTBE. The reaction was washed with aqueous saturated NH$_4$Cl, 10% aqueous citric acid, water and brine. Each aqueous phase was extracted with MTBE. Combined extracts were dried over sodium sulfate. The residue was purified by bulb-to-bulb distillation (100° C./0.1 mbar) to give a compound which was dissolved in ethanol (10 ml) and hydrogenated at ambient pressure and temperature in presence of 5% palladium on charcoal (50 mg). The product was purified by column chromatography on silica gel (eluent: heptane/ethyl acetate 99:1) followed by bulb-to-bulb distillation (90° C./0.1 mbar).

Yield: 0.44 g (98% pure; 2.1 mmol; 20%). It is a 1:1 mixture of diastereoisomers.

$^1$H-NMR: δ 0.89 (t; 3H, J 7 Hz); 1.04 (dd, J1 1.2 Hz; J2=7 Hz, 3H); 1.15-1.32 (m, 8H); 1.44 (m, 1H); 1.62 (m, 1H); 1.75 (m, 1H); 1.85-2.01 (m, 2H); 2.09 (m, 1H); 2.37 (m, 1H); 2.50 (m, 1H); 5.42 (m, 1H); 9.61 (t, J 2.2 Hz, 1H) ppm.

$^{13}$C-NMR: δ 13.20 (q); 13.40 (q); 14.14 (q); 22.97 (t); 28.29 (t); 28.36 (t); 29.18 (t); 29.23 (t); 29.25 (t); 32.07 (t); 32.12 (t); 33.30 (d); 33.37 (d); 36.06 (t); 36.11 (t); 38.94 (t); 38.97 (t); 44.34 (d); 44.41 (d); 123.59 (d); 123.64 (d); 134.04 (s); 134.06 (s); 205.36 (d); 205.37 (d) ppm.

Example 8

Synthesis of 3-(4-n-butylcyclohex-1-en-1-yl)butanal (Comparative Compound)

a) Preparation of 8-butyl-4-methyl-1-oxaspiro[4.5]decan-2-one

The procedure described for the preparation of 8-butyl-1-oxaspiro[4.5]decan-2-one (see Example 1 a)) was adapted using the following compounds and amounts:
4-n-butylcyclohexanol (46.78 g; 300 mmol); E-n-butylcrotonate (24.13 g; 166 mmol); di-tert-butyl peroxide (9.93 g; 67 mmol). The product was purified by column chromatography on silica gel (eluent: heptane/ethyl acetate 5:1 to 3:1) followed by bulb-to-bulb distillation (100° C./0.015 mbar).

Yield: 10.92 g (49 mmol; 29%). It is a mixture of 4 diastereoisomers.

$^1$H-NMR: δ0.89 (m, 3H); 1.046 (m, 3H); 1.19-1.42 (m, 9H); 1.54-1.89 (m, 6H); 2.14-2.44 (m, 2H); 2.85-2.61 (m, 1H) ppm.

$^{13}$C-NMR: δ14.10 (q); 14.11 (q); 14.33 (q); 15.44 (q); 22.89 (t); 22.93 (t); 27.98 (t); 28.24 (t); 28.88 (t); 29.04 (t); 29.16 (t); 29.52 (t); 29.57 (t); 30.48 (t); 34.25 (t); 34.35 (t); 34.83 (d); 35.60 (d); 36.09 (t); 36.46 (t); 36.62 (t); 36.83 (d); 37.36 (t); 39.75 (d); 88.10 (s); 88.54 (s); 176.14 (s); 176.29 (s) ppm.

b) Preparation of butyl 3-(4-butylcyclohex-1-en-1-yl)butanoate

The procedure described for the preparation of 3-(4-butylcyclohex-1-en-1-yl)propanoate (see example 1 b)) was adapted using the following compounds and amounts:
8-butyl-4-methyl-1-oxaspiro[4.5]decan-2-one (10.54 g; 47 mmol); 1-butanol (17.42 g; 235 mmol); concentrated sulfuric acid (0.23 g; 2.35 mmol). The product was purified by bulb-to-bulb distillation (120-160° C./0.025 mbar).

Yield: 12.91 g (46 mmol; 98%). It is a mixture of 2 diastereoisomers.

$^1$H-NMR: δ0.89 (m, 3H); 0.93 (t, J 7.4 Hz, 3H); 1.029 (dd, J1 Hz; J2=6.8 Hz, 3H); 1.11-1.31 (m, 7H); 1.33-1.46 (m, 3H); 1.59 (m, 3H); 1.72-1.78 (m, 1H); 1.97 (m, 2H); 2.07 (m, 1H); 2.24 (m, 1H); 2.41 (m, 1H); 2.56 (m, 1H); 4.05 (m, 2H); 5.41 (m, 1H).

$^{13}$C-NMR: δ 13.72 (q); 14.15 (q); 19.15 (q); 19.18 (t); 19.20 (t); 19.59 (q); 22.97 (t); 23.01 (t); 25.43 (t); 25.59 (t); 29.25 (t); 29.26 (t); 29.33 (t); 29.37 (t); 30.74 (t); 30.78 (t); 32.03 (t); 32.07 (t); 33.57 (d); 33.58 (d); 36.16 (t); 36.23 (t); 37.87 (d); 37.90 (d); 40.53 (t); 40.77 (t); 64.03 (t); 64.04 (t); 120.25 (d); 120.41 (d); 140.39 (s); 140.47 (s); 173.16 (s); 173.20 (s).

c) Preparation of 3-(4-n-butylcyclohex-1-en-1-yl)butanal

The procedure described for the preparation of 3-(4-butylcyclohex-1-en-1-yl)propanal (see Example 1 c)) was adapted using the following compounds and amounts:
butyl 3-(4-butylcyclohex-1-en-1-yl)butanoate (12.9 g; 46 mmol); diisobutylaluminum hydride (1M solution in dichloromethane, 55.2 ml, 55.2 mmol). The product was purified by column chromatography on silica gel (eluent: heptane/ethyl acetate 15:1 to 10:1) followed by bulb-to-bulb distillation (80° C./0.035 mbar). It is a mixture of 2 diastereoisomers.

Yield: 7.72 g (92% purity; 34 mmol; 74%).

¹H-NMR: δ 0.89 (broad t, J 6.9 Hz, 3H); 1.06 (d, J 6.9 Hz, 3H); 1.12-1.33 (m, 8H); 1.39-1.48 (m, 1H); 1.56-1.66 (m, 1H); 1.72-1.85 (m, 1H); 1.90-2.00 (m, 2H); 2.09 (m, 1H); 2.48 (m, 1H); 2.65 (m, 1H); 5.44 (m, 1H); 9.68 (m, 1H) ppm.
¹³C-NMR: δ 14.14 (q); 19.48 (q); 19.84 (q); 22.96 (t); 25.72 (t); 25.85 (t); 29.23 (t); 29.26 (t); 31.99 (t); 33.55 (d); 35.67 (d); 35.73 (d); 36.13 (t); 36.15 (t); 48.82 (t); 49.01 (t); 120.86 (d); 120.97 (d); 140.05 (s); 140.09 (s); 202.97 (d); 202.99 (d) ppm.

Example 9

Synthesis of 3-(4-isobutylcyclohex-1-en-1-yl)propanal (Comparative Compound)

a) Preparation of 1-(2-(1,3-dioxolan-2-yl)ethyl)-4-isobutylcyclohexan-1-ol

Under atmosphere of argon, to a suspension of magnesium turnings (2.45 g, 102 mmol) in THF (8 ml) a solution of 2-(2-bromoethyl)-1,3-dioxolane (16.8 g, 93 mmol) in THF (75 ml) was added slowly dropwise. The exotherm was maintained at 40° C. with a cooling bath. After a further 60 mins of stirring at ambient temperature a solution of the ketone prepared according to WO9955811 (9.4 g, 61 mmol) in THF (20 ml) was added slowly dropwise. After a further 15 hrs at ambient temperature, the reaction mixture was poured onto a mixture of ice and saturated ammonium chloride solution, extracted with MTBE 2×, and the combined organic phase washed with saturated sodium bicarbonate solution then brine, dried over Na₂SO₄, filtered and the solvents removed in vacuo to yield the crude alcohol 16.6 g which was used directly in the next step without further purification.

¹H-NMR: major, deduced from the mixture 80.85 (d, J=6.7, 6H); 0.93-2.10 (m, 17H); 3.83-3.88 (m, 2H); 3.95-4.00 (m, 2H); 4.88 (t, J=4.6, 1H) ppm.
¹³C-NMR: major deduced from the mixture 822.9 (2q); 24.8 (d); 27.5 (t); 28.5 (2t); 34.8 (d); 37.0 (2t); 37.8 (t); 46.5 (t); 64.9 (2t); 70.3 (s); 104.9 (d) ppm.

b) Preparation of 2-(2-(4-isobutylcyclohexan-1-en-1-yl)ethyl-1,3-dioxolane 1-(2-(1,3-dioxolan-2-yl)ethyl)-4-isobutylcyclohexan-1-ol (15.0 g, 59 mmol) was dissolved in pyridine (80 ml) and the solution cooled at 0° C. POCl₃ (15.0 g, 98 mmol) was added slowly dropwise. The solution was slowly warmed to ambient temperature and stirred for a further 18 hrs. The mixture was then cooled and poured cautiously into ice, then extracted with MTBE and the organic phase washed cautiously with saturated NaHCO₃ solution, then dilute sulfuric acid (5%, 2×), brine, dried over Na₂SO₄, filtered and the solvents removed in vacuo to yield the acetal, 11.2 g, 80%.

¹H NMR: δ 0.86 (d, J 6.5, 6H), 1.10 (t, J 6.9, 2H), 1.12-1.23 (m, 6H), 1.49-1.79 (m, 5H), 3.82-3.88 (m, 2H), 3.92-3.98 (m, 2H), 4.86 (t, J4.8, 1H), 5.36-5.42 (bs, 1H) ppm.
¹³C NMR: δ 22.7 (q), 23.1 (q), 24.9 (d), 28.5 (t), 29.6 (t), 31.0 (d), 31.9 (t), 32.2 (t), 32.2 (t), 46.1 (t), 64.8 (t), 104.5 (d), 120.6 (d), 136.8 (s) ppm;

c) Preparation of 3-(4-isobutylcyclohexan-1-en-1-yl)propanal

The crude acetal (11.9 g, 50 mmol) was dissolved in a mixture of acetone (200 ml) and water (70 ml) then HCl (concentrated, 4 ml) was added slowly and the solution heated under reflux for 4 hours then cooled. The solution was diluted with saturated NaHCO₃ solution then extracted with MTBE 2×, the combined organic phase was washed with brine, then dried over Na₂SO₄, filtered and the solvents removed in vacuo to yield the crude aldehyde, 13.0 g. Further purification by distillation (Kügelrohr, 0.7 mbar, 110-150° C.) gave the aldehyde 7.5 g. Further purification by chromatography (SiO₂) using cyclohexane:EtOAc (99:1) gave the aldehyde which was redistilled as before to give the pure 3-(4-isobutylcyclohexan-1-en-1-yl)propanal, 2.75 g, 28%.

¹H NMR: δ 0.86 (d, J 6.5, 6H), 1.10 (t, J 6.9, 2H), 1.13-1.23 (m, 1H), 1.48-1.61 (m, 2H), 1.66 (m7, J 6.9, 1H); 1.86-2.11 (m, 3H), 2.28 (t, J7.4, 2H), 2.53 (td, J7.7, 1.8 2H), 5.36-5.42 (bs, 1H) ppm.
¹³C NMR: δ 22.7 (q), 23.1 (q), 24.9 (d), 28.6 (t), 29.4 (t), 29.8 (t), 30.9 (d), 32.1 (t), 41.9 (t), 46.0 (t), 121.5 (d), 135.6 (s), 202.8 (d) ppm.

Example 10

Synthesis of 3-(4-isobutylcyclohex-1-en-1-yl)-2-methylpropanal (Comparative Compound)

a) Preparation of 1-(2-(1,3-Dioxolan-2-yl)propyl)-4-isobutylcyclohexan-1-ol 2-(2-bromoethyl)-1,3-dioxalane (20 g, 93 mmol, D. J. Collins, A. M. James, *Aust. J. Chem.* 1989, 42, 223) was added dropwise to a suspension of Mg (2.495 g, 103 mmol) in THF (100 ml) by maintaining the temperature at 15-20° C. After an additional 2 h period at 20° C., this Grignard stock reagent was 1.0 M according to titration. A solution of 4-isobutylcyclohexanone (6170 mg, 40 mmol, A. R. Pinder, *J. Chem. Soc.* 1956, 1577; M. *Julia*, C. Descoins, *Bull. Soc. Chim. Fr.* 1970, 1805) in THF (50 ml) was added dropwise to a soln. of the above Grignard reagent (1.0 M, 40 ml, 40 mmol) by maintaining the temperature below 30° C. After 18 h at 20° C., the reaction mixture was poured onto cold saturated aqueous NH₄Cl, then extracted with Et₂O. The organic phase was washed with brine, dried (Na₂SO₄), filtered and concentrated, then purified by CC/SiO₂ (cyclohexane/AcOEt 9:1) to afford 1-(2-(1,3-Dioxalan-2-yl)propyl)-4-isobutylcyclohexan-1-ol in 69% yield as a 55:45 mixture of stereoisomers.

IR: 3470, 2951, 2924, 2868, 1462, 1398, 1384, 1366, 1212, 1104, 1054, 1016, 999, 930, 870.
¹H-NMR: major δ 0.85 (d, J=6.5, 6H); 1.05 (d, J=7.2, 3H); 1.23-1.27 (m, 2H); 1.35-1.53 (m, 4H); 1.55-1.69 (m, 6H); 1.73-1.80 (m, 2H); 1.96-2.00 (m, 1H); 3.09 (brs, 1OH); 3.85-3.90 (m, 2H); 3.96-4.00 (m, 2H); 4.69 (d, J=5.2, 1H). minor δ 0.85 (d, J=6.5, 6H); 1.03 (d, J=7.2, 3H); 1.23-1.27 (m, 2H); 1.35-1.53 (m, 4H); 1.55-1.69 (m, 6H); 1.73-1.80 (m, 2H); 2.04-2.08 (m, 1H); 2.71 (brs, 1OH); 3.85-3.90 (m, 2H); 3.96-4.00 (m, 2H); 4.68 (d, J=5.2, 1H) ppm.
¹³C-NMR: major (1r,4r)-1-(2-(1,3-dioxolan-2-yl)propyl)-4-isobutylcyclohexan-1-ol δ 818.0 (q); 22.9 (2q); 25.1 (d); 26.9 (t); 30.0 (t); 31.9 (d); 34.1 (d); 36.6 (t); 39.3 (t); 45.6 (t); 45.8 (t); 64.9 (t); 65.0 (t); 71.4 (s); 108.0 (d). minor (1s,4s)-1-(2-(1,3-dioxolan-2-yl)propyl)-4-isobutylcyclohexan-1-ol δ 18.0 (q); 22.9 (2q); 24.8 (d); 28.5 (t); 28.6 (t); 31.8 (d); 34.8 (d); 36.5 (t); 38.9 (t); 45.8 (t); 46.6 (t); 64.9 (t); 65.0 (t); 70.1 (s); 108.0 (d) ppm.

b) Preparation of 2-(1-(4-Isobutylcyclohex-1-en-1-yl)propan-2-yl)-1,3-dioxolane

POCl₃ (6.27 g, 40.9 mmol) was added dropwise in 15 min. to a solution of 1-(2-(1,3-Dioxolan-2-yl)propyl)-4- isobutylcyclohexan-1-ol (7.37 g, 27.3 mmol) in pyridine (40 ml) at 0° C. After 15 min. at 0° C. and an additional 60 min. at 20° C., the reaction mixture was cooled down at 0° C. and a mixture of ice/H$_2$O (50 ml) was slowly added, followed by Et$_2$O (100 ml). After 1 h at 20° C., the reaction mixture was partitioned. The aqueous phase was washed with saturated aqueous solution of NaHCO$_3$, brine to neutrality, dried (Na$_2$SO$_4$), concentrated, and then purified by CC/SiO$_2$ (cyclohexane/AcOEt 98:2) to afford 2-(1-(4-Isobutylcyclohex-1-en-1-yl)propan-2-yl)-1,3-dioxolane in 79% yield.

IR: 2953, 2907, 2835, 1464, 1436, 1397, 1384, 1366, 1156, 1135, 1109, 1081, 1057, 1037, 998, 969, 943, 915, 801.

$^1$H-NMR: δ0.86 (d, J=6.9, 3H); 0.87 (d, J=6.2, 6H); 1.11 (t, J=7, 2H); 1.13-1.21 (m, 1H); 1.53-1.79 (m, 6H); 1.85-1.99 (m, 2H); 2.08 (brd, J=15, 1H); 2.20 (brt, J=11, 1H); 3.84-3.87 (m, 2H); 3.92-3.97 (m, 2H); 4.70 (d, J=3.8, 1H); 5.40 (s, 1H) ppm.

$^{13}$C-NMR: δ 13.1 (q); 22.7 (q); 23.1 (q); 24.9 (d); 28.4 (t); 29.6 (t); 31.1 (d); 32.2 (t); 34.7 (d); 40.0 (t); 46.2 (t); 65.1 (2t); 107.5 (d); 122.5 (d); 135.3 (s) ppm.

c) Preparation of 3-(4-Isobutylcyclohex-1-en-1-yl)-2-methylpropanal

10% HCl (5 ml) was added to a solution of 2-(1-(4-Isobutylcyclohex-1-en-1-yl)propan-2-yl)-1,3-dioxolane (5.6 g, 21.1 mmol) in THF (50 ml). After 18 h at 20° C., the reaction mixture was diluted with Et$_2$O (50 ml), and extracted with saturated aqueous solution of NaHCO$_3$, then brine. The org. phase was dried (Na$_2$SO$_4$), concentrated, and the resulting oil was purified by CC/SiO$_2$ (cyclohexane/AcOEt 97:3) to afford 3-(4-Isobutylcyclohex-1-en-1-yl)-2-methylpropanal in 48% yield. Alternatively, 5% HCl (121 ml) was added in 5 min. to a solution of 2-(1-(4-Isobutylcyclohex-1-en-1-yl)propan-2-yl)-1,3-dioxolane (21.7 g, 80 mmol) in acetone (150 ml) at 15° C. After 2 h at reflux, the cold reaction mixture was washed with sat. aq. NaHCO$_3$. The organic phase was washed with brine, dried (Na$_2$SO$_4$), concentrated, and purified by CC/SiO$_2$ (cyclohexane/AcOEt 99:1) to afford 3-(4-Isobutylcyclohex-1-en-1-yl)-2-methylpropanal in 75% yield.

IR: 2954, 2906, 2870, 2834, 2707, 1726, 1691, 1465, 1454, 1435, 1384, 1366, 1142, 915, 867, 795.

$^1$H-NMR: δ0.87 (d, J=6.8, 6H); 1.04 (d, J=7, 3H); 1.10 (t, J=7.0, 2H); 1.14-1.22 (m, 1H); 1.52-1.61 (m, 2H); 1.66 (dhept, J=6.6, 1.8, 1H); 1.70-1.75 (m, 1H); 1.87-2.00 (m, 3H); 2.08 (d, J=15.8, 1H); 2.37 (dt, J=14, 6.6, 1H); 2.51 (dhex, J=6.8, 1.8, 1H); 5.42 (m, 1H); 9.62 (d, J=1.7, 1H) ppm.

$^{13}$C-NMR: δ 13.4 (q); 22.7 (q); 23.1 (q); 24.9 (d); 28.3 (t); 29.4 (t); 30.8 (t); 32.2 (t); 38.9 (t); 44.4 (d); 46.0 (t); 123.6 (d); 134.1 (s); 205.4 (d) ppm.

Example 11

Synthesis of 3-(4-n-pentylcyclohex-1-en-1-yl)propanal (Comparative Compound)

a) Preparation of 8-n-pentyl-1-oxaspiro[4.5]decan-2-one

Following the procedure described in example 1 a), 4-n-pentylcyclohexanol (50 g; 294 mmol) was converted to 8-n-pentyl-1-oxaspiro[4.5]decan-2-one as a 3:2 mixture of diastereoisomers (5.3 g; 23 mmol; 8%).

Purified by bulb-to-bulb distillation (150° C./0.1 mbar).

$^1$H-RNM: δ 0.89 (m, 3H); 1.03 (m, 1H); 1.39-1.78 (m, 10H); 1.48 (m, 1H); 1.63 (m, 1H); 1.70-1.91 (m, 4H); 1.98 (t, J=7 Hz; 0.8H); 2.056 (t, J=7 Hz, 1.2H); 2.58 (m, 2H) ppm.

$^{13}$C-NMR: δ 14.07 (q); 14.09 (q); 22.64 (t); 22.67 (t); 26.59 (t); 26.80 (t); 28.62 (t); 28.66 (t); 29.41 (t); 30.60 (t); 32.06 (t); 32.12 (t); 34.12 (t); 34.14 (t); 35.91 (t); 35.95 (t); 36.10 (d); 36.42 (d); 36.56 (t); 36.87 (t); 85.94 (s); 87.28 (s); 176.70 (s); 176.92 (s) ppm.

b) Preparation of butyl 3-(4-n-pentylcyclohex-1-en-1-yl)propanoate

Following the procedure described in example 1 b), 8-n-pentyl-1-oxaspiro[4.5]decan-2-one (3.1 g; 13.8 mmol) was converted to 3-(4-n-pentylcyclohex-1-en-1-yl)propanoate (3.32 g; 11.8 mmol; 86%).

Purified by bulb-to-bulb distillation (150° C./0.2 mbar).

$^1$H-NMR: δ0.88 (t, J=7 Hz, 3H); 0.93 (t, J=7 Hz; 3H); 1.13-1.48 (m, 12H); 1.60 (m, 3H); 1.74 (m, 1H); 1.89-2.11 (m, 3H); 2.26 (m, 2H); 2.40 (m, 2H); 4.07 (t, J=7 Hz; 2H); 5.39 (m, 1H) ppm.

$^{13}$C-NMR: δ13.73 (q); 14.11 (q); 19.17 (t); 22.72 (t); 26.68 (t); 28.38 (t); 29.28 (t); 30.75 (t); 32.05 (t); 32.17 (t); 32.74 (t); 32.98 (t); 33.40 (d); 36.44 (t); 64.15 (t); 121.16 (d); 135.99 (s); 173.72 (s) ppm.

c) Preparation of 3-(4-n-pentylcyclohex-1-en-1-yl)propanal

Following the procedure described in example 1 c), butyl 3-(4-n-pentylcyclohex-1-en-1-yl)propanoate (3.32 g; 10.2 mmol) was converted to 3-(4-n-pentylcyclohex-1-en-1-yl)propanal (0.51 g; 2.5 mmol; 25%).

Purified by column chromatography on silica gel (eluent: heptane/ethyl acetate 99:1) followed by bulb-to-bulb distillation (125° C./1 mbar).

$^1$H-NMR: δ 9.75 (t, J=2 Hz; 1H); 5.39 (m, 1H); 2.51 (m, 2H); 2.28 (m, 2H); 2.12-1.88 (m, 3H); 1.76-1.57 (m, 3H); 1.34-1.15 (m, 9H); 0.88 t, J=7 Hz; 3H) ppm.

$^{13}$C-NMR: δ 14.11 (q); 22.71 (t); 26.67 (t); 28.59 (t); 29.23 (t); 29.87 (t); 32.02 (t); 32.15 (t); 33.39 (d); 36.41 (t); 41.92 (t); 121.53 (d); 135.60 (s); 202.75 (d).

Example 12

Synthesis of 3-(4-n-hexylcyclohex-1-en-1-yl)propanal (Comparative Compound)

a) Preparation of 8-n-hexyl-1-oxaspiro[4.5]decan-2-one

Following the procedure described in example 1 a), 4-n-hexylcyclohexanol (42 g; 228 mmol) was converted to 8-n-hexyl-1-oxaspiro[4.5]decan-2-one as a 3:2 mixture of diastereoisomers (6.8 g; 29 mmol; 13%).

Purified by bulb-to-bulb distillation (150° C./0.1 mbar).

$^1$H-NMR: δ 0.88 (t, J=7 Hz; 3H); 1.03 (m, 2H); 1.18-1.39 (m, 11H); 1.47 (m, 1H); 1.63 (m, 1H); 1.69-1.91 (m, 4H); 1.98 (t, J=7 Hz; 0.8H); 2.05 (t, J=7 Hz, 1.2H); 2.59 (m, 2H) ppm.

$^{13}$C-NMR: δ 14.11 (q); 176.67 (s); 22.66 (t); 26.89 (t); 27.11 (t); 28.62 (t); 28.66 (t); 29.42 (t); 29.53 (t); 29.57 (t); 30.61 (t); 31.86 (t); 31.89 (t); 34.15 (t); 35.96 (t); 36.10 (t); 36.44 (d); 36.61 (t); 36.88 (t); 85.92 (s); 87.27 (s); 176.67 (s); 176.89 (s) ppm.

b) Preparation of butyl 3-(4-n-hexylcyclohex-1-en-1-yl)propanoate

Following the procedure described in example 1 b), 8-n-hexyl-1-oxaspiro[4.5]decan-2-one (2.47 g; 10.4 mmol) was converted to 3-(4-n-hexylcyclohex-1-en-1-yl)propanoate (1.82 g; 6.2 mmol; 59%).

Purified by bulb-to-bulb distillation (130° C./0.2 mbar).

$^1$H-NMR: δ 0.88 (t, J=7 Hz, 3H); 0.93 (t, J=7 Hz, 3H); 1.13-1.47 (m, 12H); 1.55-1.67 (m, 4H); 1.74 (m, 1H); 1.88-2.11 (m, 4H); 2.25 (m, 2H); 2.40 (m, 2H); 4.07 (t, J=7 Hz, 2H); 5.38 (m, 1H) ppm.

$^{13}$C-NMR: δ 13.73 (q); 14.13 (q); 19.17 (t); 22.71 (t); 26.99 (t); 28.38 (t); 29.29 (t); 29.62 (t); 30.75 (t); 31.96 (t); 32.05 (t); 32.74 (t); 32.98 (t); 33.41 (d); 36.50 (t); 64.15 (t); 121.16 (d); 135.99 (s); 173.71 (s) ppm.

c) Preparation compound 3-(4-n-hexylcyclohex-1-en-1-yl)propanal

Following the procedure described in example 1 c), butyl 3-(4-n-hexylcyclohex-1-en-1-yl)propanoate (1.5 g; 5.1 mmol) was converted to 3-(4-n-hexylcyclohex-1-en-1-yl)propanal (0.6 g; 2.7 mmol; 53%).

Purified by column chromatography on silica gel (eluent: heptane/ethyl acetate 97:3) followed by bulb-to-bulb distillation (125° C./1 mbar).

$^1$H-NMR: δ0.88 (t, J=7 Hz; 3H); 1.15-1.34 (m, 11H); 1.38-1.57 (m, 2H); 1.75 (m, 1H); 1.87-2.11 (m, 3H); 2.28 (m, 2H); 2.52 (m, 2H); 5.39 (m, 1H); 9.76 (t, J=2 Hz; 1H) ppm.

$^{13}$C-NMR: δ 14.12 (q); 22.69 (t); 26.95 (t); 28.58 (t); 29.22 (t); 29.59 (t); 29.86 (t); 31.93 (t); 32.01 (t); 33.37 (d); 36.44 (t); 41.91 (t); 121.54 (d); 135.60 (s); 202.83 (d) ppm.

Example 13

Preparation of a Perfuming Composition

A perfuming composition for liquid detergent was prepared by admixing the following ingredients:

| Ingredient | Parts by weight |
| --- | --- |
| Benzyl acetate | 200 |
| (2E)-2-benzylideneoctanal | 600 |
| (+−)-2-methylundecanal | 200 |
| Cetalox ®[1] | 40 |
| (+−)-3,7-Dimethyl-6-octen-1-ol | 600 |
| 4-cyclohexyl-2-methyl-2-butanol | 1000 |
| Verdyl Propionate[2] | 800 |
| (+−)-2,6-dimethyl-7-octen-2-ol | 2000 |
| (+−)-(1-ethoxyethoxy)cyclododecane[3] | 200 |
| (E)-3,7-dimethyl-2,6-octadien-1-ol | 200 |
| Helvetolide ®[4] | 400 |
| Iso E Super ®[5] | 800 |
| Lilyflore ®[6] | 200 |
| Hedione ®[7] | 150 |
| Neobutenone ® alpha[8] | 10 |
| Norlimbanol ® dextro[9] | 40 |
| (2RS,4SR)-4-methyl-2-(2-methyl-1-propen-1-yl) tetrahydro-2H-pyran and (2RS,4RS)-4-methyl-2-(2-methyl-1-propen-1-yl)tetrahydro-2H-pyran | 10 |
| (+−)-3-methyl-5-phenyl-1-pentanol | 200 |
| Hexyl 2-hydroxybenzoate | 1000 |
| (+−)-2-ethyl-4,4-dimethylcyclohexanone | 10 |
| Veloutone ®[10] | 40 |
| Verdox ™[11] | 1200 |
|  | 9900 |

[1] (3ars,5asr,9asr,9brs)-3a,6,6,9a-tetramethyldodecahydronaphtho[2,1-b]furan; origin: Firmenich SA, Geneva, Switzerland
[2] Origin: Givaudan-Roure SA, Vernier, Suisse
[3] Origin: Firmenich SA, Geneva, Switzerland
[4] (+)-(1s,1'r)-2-[1-(3',3'-dimethyl-1'-cyclohexyl)ethoxy]-2-methylpropyl propanoate; Origin: Firmenich SA, Geneva, Switzerland
[5] 1-(octahydro-2,3,8,8-tetramethyl-2-naphtalenyl)-1-ethanone; origin: International Flavors & Fragrances, USA
[6] (+−)-2,5-dimethyl-2-indanmethanol; origin: Firmenich SA, Geneva, Switzerland
[7] Methyl 2-((1RS,2RS)-3-oxo-2-pentylcyclopentyl)acetate; origin: Firmenich SA, Geneva, Switzerland
[8] 1-(5,5-dimethyl-1-cyclohexen-1-yl)-4-penten-1-one; origin: Firmenich SA, Geneva, Switzerland
[9] trans-1-(2,2,6-trimethyl-1-cyclohexyl)-3-hexanol; origin: Firmenich SA, Geneva,Switzerland
[10] (+−)-2,2,5-trimethyl-5-pentylcyclopentanone; origin: Firmenich SA, Geneva, Switzerland
[11] 2-tert-butyl-1-cyclohexyl acetate; origin: International Flavors & Fragrances, USA 1) (3ars,5asr,9asr,9brs)-3a,6,6,9a-tetramethyldodecahydronaphtho[2,1-b]furan; origin: Firmenich SA, Geneva, Switzerland
2) Origin: Givaudan-Roure SA, Vernier, Suisse
3) Origin: Firmenich SA, Geneva, Switzerland
4) (+)-(1s,1'r)-2-[1-(3',3'-dimethyl-1'-cyclohexyl)ethoxy]-2-methylpropyl propanoate; Origin: Firmenich SA, Geneva, Switzerland
5) 1-(octahydro-2,3,8,8-tetramethyl-2-naphtalenyl)-1-ethanone; origin: International Flavors & Fragrances, USA
6) (+−)-2,5-dimethyl-2-indanmethanol; origin: Firmenich SA, Geneva, Switzerland
7) Methyl 2-((1RS,2RS)-3-oxo-2-pentylcyclopentyl)acetate; origin: Firmenich SA, Geneva, Switzerland
8) 1-(5,5-dimethyl-1-cyclohexen-1-yl)-4-penten-1-one; origin: Firmenich SA, Geneva, Switzerland
9) trans-1-(2,2,6-trimethyl-1-cyclohexyl)-3-hexanol; origin: Firmenich SA, Geneva, Switzerland
10) (+−)-2,2,5-trimethyl-5-pentylcyclopentanone; origin: Firmenich SA, Geneva, Switzerland
11) 2-tert-butyl-1-cyclohexyl acetate; origin: International Flavors & Fragrances, USA The addition of 100 parts by weight of 3-(4-n-butyl-1-cyclohexen-1-yl)propanal to the above-described composition imparted to the latter a creamy, petallic and mandarin note with also coriander aspect while providing freshness to the composition. The composition acquired more volume and becomes very powerful. 3-(4-n-butyl-1-cyclohexen-1-yl)propanal blends particularly well with the clean-aldehydic elements such as (+−)-2-methylundecanal and with floral elements such as (+−)-3,7-Dimethyl-6-octen-1-ol, (E)-3,7-dimethyl-2,6-octadien-1-ol and Lilyflore of the composition When instead of the invention's compound, the same amount of Mugoxal® (3-(4-tert-butyl-1-cyclohexen-1-yl) propanal; origin: Firmenich SA, Geneva, Switzerland) was used, the composition acquired a more floral/lily of the valley connotation allied with citrus facet but devoid of creamy, petallic, mandarin and coriander note. Moreover, said composition is less strong.

When instead of the invention's compound, the same amount of Starfleur® (3-[4-(2-Methylpropyl)cyclohexyl] propanal; origin: International Flavors & Fragrances, USA) was used, the results was totally different as the composition acquired an aldehydic, citronella note. Said composition was weaker and less clean with metallic and dusty note. When instead of the invention's compound, the same amount of 3-(4-isobutylcyclohexyl)-2-methylpropanal, the composition only acquired aldehydic note. Said composition was the weakest.

When instead of the invention's compound, the same amount of 3-(4-n-butylcyclohexyl) propanal was used, the composition becomes fattier, more metallic and slightly animal-fecal.

The composition comprising 3-(4-n-butyl-1-cyclohexen-1-yl)propanal is the most powerful. After 24 h, said composition is still the strongest with effects on the top note still present.

Example 14

Preparation of a Liquid Detergent Comprising the Invention's Compound

TABLE 2

Composition of the liquid detergent formulation

| Ingredients | Concentration [wt %] |
|---|---|
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Properase L[4] | 0.2 |
| Puradax EG L[4] | 0.2 |
| Purastar ST L[4] | 0.2 |
| Acrylates/Stareth-20 Methacrylate structuring Crosspolymer[5] | 6 |
| Deionized Water | 27.4 |

[1] Hostapur SAS 60; Origin: Clariant
[2] Edenor K 12-18; Origin: Cognis
[3] Genapol LA 070; Origin: Clariant
[4] Origin: Genencor International
[5] Aculyn 88; Origin: Dow Chemical The liquid detergent was prepared by adding 1.5% by weight, relative to the total weight of the liquid detergent, of the invention's composition of example 13 into the unperfumed liquid detergent formulation of Table 2 under gentle shaking.

Example 15

Preparation of a Fabric Softener Comprising the Invention's Compound

TABLE 3

Composition of the softener formulation

| Ingredient | Concentration [wt %] |
|---|---|
| Methyl bis[ethyl (tallowate)]-2-hydroxyethyl ammonium methyl sulfate[1] | 12.20 |
| 1,2-benzisothiazolin-3-one[2] | 0.04 |
| CaCl$_2$ (10% aqueous solution) | 0.40 |
| Water | 87.36 |

[1] Stepantex VL90 A Diester Quat; Origin: Stepan
[2] Proxel GXL; Origin: Arch

The softener was prepared by weighting Methyl bis[ethyl (tallowate)]-2-hydroxyethyl ammonium methyl sulfate which was heated at 65° C. Then Water and 1,2-benzisothiazolin-3-one were placed in the reactor and were heated at 65° C. under stirring. To the above mixture was added Methyl bis[ethyl (tallowate)]-2-hydroxyethyl ammonium methyl sulfate. The mixture was stirred 15 minuted and CaCl$_2$ was added. Then 0.5 to 2% by weight, relative to the total weight of the softener, of the invention's composition of example 13 was added. The mixture was stirred 15 minutes and was cooled down to room temperature under stirring (viscosity measure: result 35+/−5 mPas. (shear rate 106 sec-1)).

Example 16

Preparation of a Transparent Isotropic Shampoo Comprising the Invention's Composition

TABLE 4

Composition of the transparent isotropic shampoo formulation

| Phases | Ingredients | Concentration [wt %] |
|---|---|---|
| A | Water deionized | 44.4 |
|  | Polyquaternium-10[1] | 0.3 |
|  | Glycerin 85%[2] | 1 |
|  | DMDM Hydantoin[3] | 0.2 |
| B | Sodium Laureth Sulfate[4] | 28 |
|  | Cocamidopropyl Betaine[5] | 3.2 |
|  | Disodium Cocoamphodiacetate[6] | 4 |
|  | Ethoxy (20) Stearyl Alcohol[6] | 1 |
| C | Sodium Laureth Sulfate[4] | 3 |
|  | Glyceryl Laureate[7] | 0.2 |
| D | Water deionized | 1 |
|  | Sodium Methylparaben[8] | 0.1 |
| E | Sodium Chloride 10% aqueous sol. | 15 |
|  | Citric acid 10% aqueous sol. till pH 5.5-6 | q.s. |

[1] Ucare Polymer JR-400, Origin: Noveon
[2] Origin: Schweizerhall
[3] Glydant, Origin: Lonza
[4] Texapon NSO IS, Origin: Cognis
[5] Tego Betain F 50, Origin: Evonik
[6] Amphotensid GB 2009, Origin: Zschimmer & Schwarz
[7] Monomuls 90 L-12, Origin: Gruenau
[8] Nipagin Monosodium, Origin: NIPA The shampoo was prepared by dispersed in water Polyquaternium-10. The remaining ingredients of phase A were mixed separately by addition of one after the other while mixing well after each adjunction. This pre-mix was added to the Polyquaternium-10 dispersion and mixed for another 5 min. Then, the premixed phase B and the premixed Phase C were added (Monomuls 90L-12 was heated to melt in Texapon NSO IS) while agitating. Phase D and Phase E were added while agitating. PH was adjusted with citric acid solution till pH: 5.5-6.0 leading to an unperfumed shampoo formulae.

The perfumed shampoo was prepared by adding 0.4 to 0.8% by weight, relative to the total weight of the shampoo, of the invention's composition of example 13 into the unperfumed shampoo formulation of Table 4 under gentle shaking.

Example 17

Preparation of a Structured Shower Gel Comprising the Invention's Composition

TABLE 5

Composition of the shower gel formulation

| Ingredients | Amount (% wt) |
|---|---|
| WATER deionised | 49.350 |
| Tetrasodium EDTA[1] | 0.050 |
| Acrylates Copolymer[2] | 6.000 |

TABLE 5-continued

Composition of the shower gel formulation

| Ingredients | Amount (% wt) |
|---|---|
| Sodium C12-C15 Pareth Sulfate[3] | 35.000 |
| Sodium Hydroxide 20% aqueous solution | 1.000 |
| Cocamidopropyl Betaine[4] | 8.000 |
| Methylchloroisothiazolinone and Methylisothiazolinone[5] | 0.100 |
| Citric Acid (40%) | 0.500 |

[1]EDETA B POWDER; trademark and origin: BASF
[2]CARBOPOL AQUA SF-1 POLYMER; trademark and origin: NOVEON
[3]ZETESOL AO 328 U; trademark and origin: ZSCHIMMER & SCHWARZ
[4]TEGO-BETAIN F 50; trademark and origin: GOLDSCHMIDT
[5]KATHON CG; trademark and origin: ROHM & HASS The shower gel was prepared by adding 0.5 to 1.5% by weight, relative to the total weight of the shower gel, of the invention's composition of example 13 into the unperfumed shower gel formulation of Table 5 under gentle shaking.

Example 18

Preparation of a Transparent Shower Gel Comprising the Invention's Composition

TABLE 6

Composition of the transparent shower gel formulation

| Ingredients | Concentration (% wt) |
|---|---|
| WATER deionized | 52.40 |
| Tetrasodium EDTA[1] | 0.10 |
| Sodium Benzoate | 0.50 |
| Propylene Glycol | 2.00 |
| Sodium C12-C15 Pareth Sulfate[2] | 35.00 |
| Cocamidopropyl Betaine[3] | 8.00 |
| Polyquaternium-7[4] | 0.20 |
| Citric Acid (40%) | 1.00 |
| Sodium Chloride | 0.80 |

[1]EDETA B POWDER; trademark and origin: BASF
[2]ZETESOL AO 328 U; trademark and origin: ZSCHIMMER & SCHWARZ
[3]TEGO-BETAIN F 50; trademark and origin: GOLDSCHMIDT
[4]MERQUAT 550; trademark and origin: LUBRIZOL The transparent shower gel was prepared by adding 0.5 to 1.5% by weight, relative to the total weight of the shower gel, of the invention's composition of example 13 into the unperfumed shower gel formulation of Table 6 under gentle shaking.

Example 19

Preparation of a Milky Shower Gel Comprising the Invention's Composition

TABLE 7

Composition of the milky shower gel formulation

| Ingredients | Concentration (% wt) |
|---|---|
| WATER deionized | 50.950 |
| Tetrasodium EDTA[1] | 0.050 |
| Sodium Benzoate | 0.500 |
| Glycerin 86% | 3.500 |
| Sodium Laureth Sulfate[2] | 27.000 |
| Polyquaternium-7[3] | 1.000 |
| Coco-Betaine[4] | 6.000 |
| PEG-120 Methyl Glucose trioleate[5] | 1.000 |
| Citric Acid (40%) | 1.000 |

TABLE 7-continued

Composition of the milky shower gel formulation

| Ingredients | Concentration (% wt) |
|---|---|
| Glycol Distearate & Laureth-4 & Cocamidopropyl Betaine[6] | 3.000 |
| Sodium Chloride 20% | 5.000 |
| PEG-40 Hydrogenated Castor Oil[7] | 1.000 |

[1]EDETA B POWDER; trademark and origin: BASF
[2]Texapon NSO IS; trademark and origin: COGNIS
[3]MERQUAT 550; trademark and origin: LUBRIZOL
[4]DEHYTON AB-30; trademark and origin: COGNIS
[5]GLUCAMATE LT; trademark and origin: LUBRIZOL
[6]EUPERLAN PK 3000 AM; trademark and origin: COGNIS
[7]CREMOPHOR RH 40; trademark and origin: BASF The transparent shower gel was prepared by adding 0.5 to 1.5% by weight, relative to the total weight of the shower gel, of the invention's composition of example 13 into the unperfumed shower gel formulation of Table 7 under gentle shaking.

Example 20

Preparation of a Pearly Shampoo Comprising the Invention's Composition

TABLE 8

Composition of the pearly isotropic shampoo formulation

| Phases | Ingredients | Concentration (% wt) |
|---|---|---|
| A | Water deionized | 45.97 |
|   | Tetrasodium EDTA[1] | 0.05 |
|   | Guar Hydroxypropyltrimonium Chloride[2] | 0.05 |
|   | Polyquaternium-10[3] | 0.075 |
| B | NaOH 10% aqueous sol. | 0.3 |
| C | Ammonium Lauryl Sulfate[4] | 34 |
|   | Ammonium Laureth Sulfate[5] | 9.25 |
|   | Cocamidopropyl Betaine[6] | 2 |
|   | Dimethicone (&) C12-13 Pareth-4 (&) C12-13 Pareth-23 (&) Salicylic Acid[7] | 2.5 |
| D | Cetyl Alcohol[8] | 1.2 |
|   | Cocamide MEA[9] | 1.5 |
|   | Glycol Distearate[10] | 2 |
| E | Methylchloroisothiazolinone & Methylisothiazolinone[11] | 0.1 |
|   | D-Panthenol 75%[12] | 0.1 |
|   | Water deionized | 0.3 |
| F | Sodium Chloride 25% aqueous sol. | 0.6 |

[1]EDETA B Powder, Origin: BASF
[2]Jaguar C14 S, Origin: Rhodia
[3]Ucare Polymer JR-400, Origin: Noveon
[4]Sulfetal LA B-E, Origin: Zschimmer & Schwarz
[5]Zetesol LA, Origin: Zschimmer & Schwarz
[6]Tego Betain F 50, Origin: Evonik
[7]Xiameter MEM-1691, Origin: Dow Corning
[8]Lanette 16, Origin: BASF
[9]Comperlan 100, Origin: Cognis
[10]Cutina AGS, Origin: Cognis
[11]Kathon CG, Origin: Rohm & Haas
[12]D-Panthenol, Origin: Roche The shampoo was prepared by dispersed in water and Tetrasodium EDTA, Guar Hydroxypropyltrimonium Chloride and Polyquaternium-10. NaOH 10% solution (Phase B) was added once Phase A was homogeneous. Then, the premixed Phase C was added. and mixture was heated to 75° C. Phase D ingredients were added and mixed till homogeneous. The mixture was cooled down. At 45° C., Phase E ingredients were added while mixing. Final viscosity was adjusted with 25% NaCl solution and pH of 5.5-6 was adjusted with 10% NaOH solution.

The perfumed pearly shampoo was prepared by adding 0.4 to 0.8% by weight, relative to the total weight of the shampoo, of the invention's composition of example 13 into the unperfumed shampoo formulation of Table 8 under gentle shaking.

Example 21

Preparation of a Structured Shower Gel Comprising the Invention's Composition

TABLE 9

Composition of the milky shower gel formulation

| Ingredients | Amount (% wt) |
|---|---|
| WATER deionised | 49.350 |
| Tetrasodium EDTA[1) | 0.050 |
| Acrylates Copolymer[2) | 6.000 |
| Sodium C12-C15 Pareth Sulfate[3) | 35.000 |
| Sodium Hydroxide 20% aqueous solution | 1.000 |
| Cocamidopropyl Betaine[4) | 8.000 |
| Methylchloroisothiazolinone and Methylisothiazolinone[5) | 0.100 |
| Citric Acid (40%) | 0.500 |

[6)EDETA B POWDER; trademark and origin: BASF
[7)CARBOPOL AQUA SF-1 POLYMER; trademark and origin: NOVEON
[8)ZETESOL AO 328 U; trademark and origin: ZSCHIMMER & SCHWARZ
[9)TEGO-BETAIN F 50; trademark and origin: GOLDSCHMIDT
[10)KATHON CG; tradeark and origin: ROHM & HASS The transparent shower gel was prepared by adding 0.5 to 1.5% by weight, relative to the total weight of the shower gel, of the invention's composition of example 13 into the unperfumed shower gel formulation of Table 9 under gentle shaking.

Example 22

Preparation of a Eau De Toilette Comprising the Invention's Compound

The eau de toilette was prepared by adding 5 to 20% by weight, relative to the total weight of the eau de toilette, of the invention's composition of example 13 into ethanol under gentle shaking.

The invention claimed is:
1. A method of using a compound of formula (I)

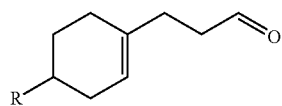

(I)

in the form of any one of its stereoisomers or as a mixture thereof, wherein R represents a n-butyl or a (3-methylbutan-2-yl) group, the method comprising using the compound as a perfuming ingredient to impart odor notes comprising an aldehydic facet of a lily of the valley odor note and creamy and coriander odor notes.

2. The method according to claim 1, wherein R represents a n-butyl group.

3. A method to confer, enhance, improve or modify the odor properties of a perfuming composition or of a perfumed article, the method comprising adding to the perfuming composition or the perfumed article an effective amount of at least a compound of formula (I) as defined in claim 1.

4. A compound of formula (I) as defined in claim 1.

5. A perfuming composition comprising:
   i) at least one compound of formula (I), as defined in claim 4;
   ii) at least one ingredient selected from the group consisting of a perfumery carrier and a perfumery base; and
   iii) optionally at least one perfumery adjuvant.

6. A perfumed consumer product comprising a composition as defined in claim 5.

7. A perfumed consumer product comprising at least one compound of formula (I), as defined in claim 4.

8. The perfumed consumer product according to claim 7, wherein the perfumed consumer product is a perfume, a fabric care product, a body-care product, a cosmetic preparation, a skin-care product, an air care product, or a home care product.

9. The perfumed consumer product according to claim 8, wherein the perfumery consumer product is a fine perfume, a splash or eau de perfume, a cologne, a shave or after-shave lotion, a liquid or solid detergent, a fabric softener, a fabric refresher, an ironing water, a paper, a bleach, a carpet cleaner, curtain—care products, a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, a foot/hand care products, a hygiene product, an air freshener, a "ready to use" powdered air freshener, a mold remover, furnisher care, wipe, a dish detergent or hard-surface detergent, a leather care product, or a car care product.

\* \* \* \* \*